(12) United States Patent
Sapiens et al.

(10) Patent No.: US 11,484,196 B2
(45) Date of Patent: *Nov. 1, 2022

(54) METHOD AND APPARATUS FOR REFRACTION AND VISION MEASUREMENT

(71) Applicant: EyeQue Inc., Newark, CA (US)

(72) Inventors: Noam Sapiens, Newark, CA (US); John Serri, Newark, CA (US); Johan Borglin, Newark, CA (US)

(73) Assignee: EyeQue Inc., Newark, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/935,815

(22) Filed: Jul. 22, 2020

(65) Prior Publication Data

US 2020/0352436 A1 Nov. 12, 2020

Related U.S. Application Data

(63) Continuation-in-part of application No. 16/809,482, filed on Mar. 4, 2020, and a continuation-in-part of application No. 16/685,017, filed on Nov. 15, 2019, application No. 16/809,482, which is a continuation-in-part of application No. 16/276,302, filed on Feb. 14, 2019, now Pat. No. 10,588,507.
(Continued)

(51) Int. Cl.
*A61B 3/103* (2006.01)
*G01M 11/02* (2006.01)

(52) U.S. Cl.
CPC ......... *A61B 3/103* (2013.01); *G01M 11/0228* (2013.01)

(58) Field of Classification Search
CPC ............... A61B 3/103; A61B 3/02–09; A61B 3/10–165; A61B 3/032; A61B 3/0025; A61B 3/0033; A61B 3/0041; A61B 3/0091; G01M 11/0228
USPC .................................. 351/222–244, 205–221
See application file for complete search history.

(56) References Cited

U.S. PATENT DOCUMENTS 10,588,507 B2 * 3/2020 Skolianos ............... A61B 3/103
2013/0027668 A1 * 1/2013 Pamplona .............. A61B 3/032
351/239

(Continued)

*Primary Examiner* — Cara E Rakowski
(74) *Attorney, Agent, or Firm* — Steven A. Nielsen; www.NielsenPatents.com (57) ABSTRACT

Consumer products such as refraction measurement devices may be used for obtaining refraction measurements allow consumers to track their vision without visiting an optometrist or ophthalmologist. Such consumer products may work in concert with smart phones or other products having a touch screen that present images to refraction measurement devices. Smart phones may have resolution rates, sometimes measured as PPI or pixels per inch that are unknown to the user and/or refraction measurement device. One aspect of the invention is to provide an optical interface for the user to manually match the view port boundary of the smartphone to comport with the view port boundary of the refraction measurement device. Another aspect of the invention is the use of pre-distortion in images presented to the user. By noting the corrective movements exerted by the user upon the refractive measurement device, the user's own refractive error can be derived.

7 Claims, 5 Drawing Sheets

Related U.S. Application Data application No. 16/685,017, which is a continuation-in-part of application No. 16/276,302, filed on Feb. 14, 2019, now Pat. No. 10,588,507, application No. 16/935,815, which is a continuation-in-part of application No. 16/176,631, filed on Oct. 31, 2018, said application No. 16/276,302 is a continuation-in-part of application No. 15/491,557, filed on Apr. 19, 2017, now Pat. No. 10,206,566.

(60) Provisional application No. 62/876,889, filed on Jul. 22, 2019, provisional application No. 62/579,558, filed on Oct. 31, 2017, provisional application No. 62/409,276, filed on Oct. 17, 2016.

(56) References Cited

U.S. PATENT DOCUMENTS

| | | | |
|---|---|---|---|
| 2013/0092816 A1* | 4/2013 | Barrett | G01J 9/00 250/201.9 |
| 2016/0157716 A1* | 6/2016 | Pamplona | A61B 3/103 351/213 |
| 2016/0242644 A1* | 8/2016 | Winsor | A61B 3/14 |
| 2020/0008667 A1* | 1/2020 | Raviv | A61B 3/113 |
| 2021/0275012 A1* | 9/2021 | Prevoo | A61B 3/0041 |

* cited by examiner

METHOD AND APPARATUS FOR REFRACTION AND VISION MEASUREMENT

CROSS-REFERENCE TO RELATED APPLICATIONS

This application is a continuation or continuation in part of the following patent applications, the contents of which are incorporated herein by reference:

U.S. patent application Ser. No. 16/685,017, Automated Personal Vision Tracker, filed on filed on Nov. 15, 2019, which is a continuation in part of U.S. patent application Ser. No. 16/276,302 Optical Method to Assess the Refractive Properties of an Optical System filed on Feb. 14, 2019 which is now U.S. Pat. No. 10,488,507 which is a continuation in part of U.S. patent application Ser. No. 15/491,557 filed on Apr. 19, 2017, not U.S. Pat. No. 10,206,566 which claims priority for provisional patent application 62/409,276 filed on Oct. 17, 2016.

This application is a continuation in part of U.S. patent application Ser. No. 16/176,631 Smart Phone Based Virtual Visual Charts for Measuring Visual Acuity filed on Oct. 31, 2018 which claims a priority date of Oct. 31, 2017 from provisional patent application 62/579,558.

This application claims the benefit of provisional patent application 62/876,889 filed on Jul. 22, 2019.

Not Applicable

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever. Such trademarks may include "EyeQue", "PVT" "Personal Vision Tracker", "Insight", "VisionCheck" and others.

BACKGROUND OF THE INVENTION

Vision is arguably the most important of the senses. The human eye and its direct connection to the human brain is an extremely advanced optical system. Light from the environment goes through the eye optical train comprised of the cornea, the pupil, and the lens and focuses to create an image on the retina. As all optical systems, light propagation through the eye optics is subject to aberrations. The most common forms of aberrations in the eye are defocus and astigmatism. These low order aberrations are the cause of the most common refractive eye conditions myopia (near-sightedness) and hyperopia (farsightedness). Higher order aberrations are also present and can be described most conveniently by the Zernike polynomials. These usually have a lower effect on visual function. The eye, like any other organ in the human body, may suffer from various diseases and disorders, the most prominent today are: cataract, AMD, glaucoma, diabetic retinopathy, dry eye. Other conditions exist and should also be considered in the scope of this application.

Ophthalmic measurements are critical for eye health and proper vision. Those ophthalmic measurements could be sectioned into objective and subjective types. Objective types measurements give a metric of a physiological, physical (e.g. mechanical or optical), biological or functional without the need for input from the measured individual (patient, subject, user or consumer). Examples of objective tests include but are not limited to OCT (optical coherent tomography used to image a 3 dimensional and cross sections of the eye), scanning laser ophthalmoscope (SLO, used for spectral imaging of the retina), fundus image (used to present an image of the retina), auto-refractor (used for refraction measurement), keratometer (used for providing a profile of the cornea), tonometer (used to measure the IOP—intra ocular pressure). Subjective measurements give a metric with relation to the individual input. That is, they provide parameters that also take into consideration the brain functions, perception and cognitive abilities of the individual. Examples of subjective tests include but are not limited to visual acuity test, contrast sensitivity test, phoropter refraction test, color vision test, visual field test, and the EyeQue PVT and Insight.

Today, both objective and subjective eye exams (measurements) are done by an ophthalmologist or an optometrist. The process usually involves the patient needing to schedule an appointment, wait for the appointment, travel to the appointment location (e.g. office or clinic), wait in line, perform multiple tests using various tools and potentially moving between different technicians and different eye doctors. The prolonged wait times both for the appointment as well as in line at the appointment location, along with the hassle of performing the tests with different professionals and the duration of those tests might seem daunting to many patients. Furthermore, the shear effort associated with the process and even the requirement of remembering to start the process to begin with might deter patients from going through with it.

Moreover, currently about 2.5 billion people do not have access to eye and vision care at all. The cost of eye exams could be considered quite significant especially in some places in the world. This poses a hindrance to the availability of eye care in third world countries for example. The cost, time consumption and perceived hassle also makes it at times prohibitive to have repeated eye exams, especially at the desired frequency. Those might be necessary in special cases (for example after refractive surgery or cataract surgery where repeated measurements should be performed to track the progress of the patient's status over time and the success of the surgery. Additionally, even under normal circumstances, measurements at a doctor's office only represent a single point in time. The situation under which the measurements were made might not be optimal or do not fully represent the patient's characteristics. The patient might have been tired, stressed or agitated (a doctor's visit might be quite stressful in and of itself but could also being run from test to test and being posed with questions and options elevate the patient's level of stress) or was just in a bad mood. Even the state of mind of the doctor themselves might influence the way the measurement is performed. Beyond all that, the time of day and other environmental conditions (whether direct e.g. lighting conditions or indirect e.g. temperature) could also affect the measurement and provide incomplete or false information.

The availability of information (including specifically medical information) on the internet, the increased awareness of people for preventive medicine, and the emergence of tele-medicine leads to many taking control of their own health. Devices for screening, monitoring and tracking medical conditions are quite pervasive in today's world, for example blood pressure measurement devices, and blood sugar monitors. The technological advancements allow for people to be more independent in diagnosis, prevention and tracking of various health conditions. Furthermore, many prefer to perform these activities in the comfort of their homes without the need for appointments or other time-consuming activities. In case of an anomaly, they would call or email their physicians to consult for the appropriate course of action.

The advancement of technologies effectively makes computers with screens and cameras ubiquitous in the form of laptops, tablets and smartphones. Therefore, enabling many people to have a device already capable of computing displaying and recording information.

All this brings the need for a series of devices that will enable users to perform ophthalmic measurements at home, by themselves, in a timely and cost-effective manner. It should be clear that the quality of these measurements and their accuracy and precision should meet or exceed the standards of today's measurement methods.

This vision could be further enhanced by use of cloud-based data and analytics that enables complete access to the entire history of a patient exams, tests and measurements. Moreover, the use of artificial intelligence (AI) will enable diagnosis based on machine learning and big data. This could be done by means of data mining, neural network decision making and pattern detection and recognition, as some examples of the AI capabilities.

To summarize, the vision for eye care in the not so far future will look like: A complete solution for eye and vision care for consumers and doctors; Remote, self-administered battery of tests for both disease and functional; measurements are enabled by technology and devices, AI is used for analysis, tracking and reporting. Enhanced by big data correlations and insights.

In simple terms, as an example: A person sits on their couch at the comfort of their home, uses a device to do various measurements, that data is uploaded to an AI for analysis. The AI will let the person know the results and notify the doctor. The AI will initiate alerts for the person and doctor in necessary cases. The person will not need to get up unless a serious issue occurs (i.e. surgery). All other issues will be dealt with remotely (e.g. email/phone/video conference with the doctor, order glasses and have them delivered to the home, direct delivery of doctor prescribed medications).

Despite the apparent approach of "direct to consumer", the methodologies could easily be implemented for a more enterprise like model. One example of such implementation will have a hierarchical structure in which an entity such as a hospital, association, or a medical insurance company provides the ability for the doctors to provide their patients with such devices and capabilities. The devices are all connected through the user accounts to the cloud and the measurements are streamed directly into the users' accounts (and potentially their medical records). Those accounts could be attached to one or more doctors and can also be transferred and shared.

(1) Field of the Invention

The invention generally relates to vision testing and refraction measurement systems that attach to a display for example the PVT system, the VisionCheck system and the Insight systems by EyeQue. More particularly, the invention relates to means and methods of measuring characteristics of the display and correcting for optical aberrations in the abovementioned systems. Any system intended for measurement of vision and ocular characteristics (e.g. refraction), where the system includes a display, an optical system comprised of refractive elements and/or reflective elements (e.g. lenses and/or mirrors) may suffer from two main problems: the characteristics of the display may not be known (e.g. where the display may be part of a smartphone and the phone resolution is not well reported), and the optical system creates aberrations for the displayed image. The proposed invention describes methods and apparatuses for overcoming these problems.

(2) Description of the Related Art

The known related art fails to anticipate or disclose the principles of the present invention.

In the related art, minimization of the FoV and more particularly in the PVT system the images size, allows a way to overcome the distortion aberration in the system that causes the presented image to form bent lines to the user while having straight lines on the display. The VisionCheck system incorporates an aspheric lens to overcome the distortion of the lines presented to the user. This type of hardware solution makes the system more complicated and expensive.

The display property of PPI is crucial in the determination of the presented image size. Scaling needs to be done between different displays to allow for correct representation of the images. The current systems rely on the input from the phone firmware to indicate the correct resolution in the form of the PPI (pixels per inch). Some phones today do not report that value correctly. It is therefore necessary for these phone displays to manually input the correct PPI in the backend of the software.

Thus, there is a long felt need in the art for the present invention.

BRIEF SUMMARY OF THE INVENTION

The present invention overcomes shortfalls in the related art by presenting an unobvious and unique combination and configuration of methods and components to correct for optical aberrations in the system and to allow a self-calibration method to measure the display resolution.

The invention overcomes shortfalls in the related art by using calibration processes to measure the display resolution and create a correction mapping of the distortion aberration.

In an embodiment of the invention the display is part of a smartphone. The user is presented with a rectangle of the right aspect ratio as the attached device. The attached device dimensions are well known. The user then adjusts and aligns the rectangle on the screen to match the attachment outline of the device. The known size of the device and the input rectangle size in pixels can then be used to calculate the phone resolution or more specifically its PPI (Pixels Per Inch). This could then be used for alignment and scaling of images on the display. In turn, this could be used for performing vision and refraction measurements.

In another embodiment of the invention the resolution measurement is based on the use of external sensor input. An example of the embodiment could be implemented using a smartphone as the display device. The attached system could then have touch points of known and defined distance. When the attached system is physically attached to the phone, the touch points indicate the pixel location of those touch points which in turn may be used in conjunction with the known distance between the points to calculate the display resolution and PPI.

In another embodiment of the invention, an optical system is attached to a display. The display presents images to the user. These images can be used for vision tests or as means to measure an optical system refraction. As an example, the optical system could be a user's eye and the refraction measurement could be the eye's required refractive correction. The optical system introduces aberrations to the user, specifically distortion aberration. This causes the image to look unclear and malformed. A method is presented in the invention to resolve the image distortion by means of pre-distortion of the image on the display. An image is pre-distorted with a distortion that is opposite that is introduced by the optical system so that, if observed on the display directly will look deformed and while looking through the optical system with its inherent distortion will cause the image to look sharp and without misshape. The main principle of the pre-distortion is a spatially dependent image curvature calibrated based on the original system distortion map.

These and other objects and advantages will be made apparent when considering the following detailed specification when taken in conjunction with the drawings.

REFERENCE NUMERALS IN THE DRAWINGS

100 current listing of steps to obtain eye glasses
200 proposed steps of obtaining eyeglasses
300 attachment device, such as a Personal Vision Tracker
320 straight lines spaced apart as observed through an attachment device as a result of using a pre-distorted image 490
350 straight lines disposed upon one another as a result of user adjustments of the attached device
400 display device, such as a smart phone
430 view port indicia for a user to adjust to comport with an attached device
480 image presented upon a display device, such as a smart phone
490 pre-distorted image presented by the smartphone
500 alternative attachment device, such as an Insight
540 input area of attached device
560 touch points

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

Figure 1:
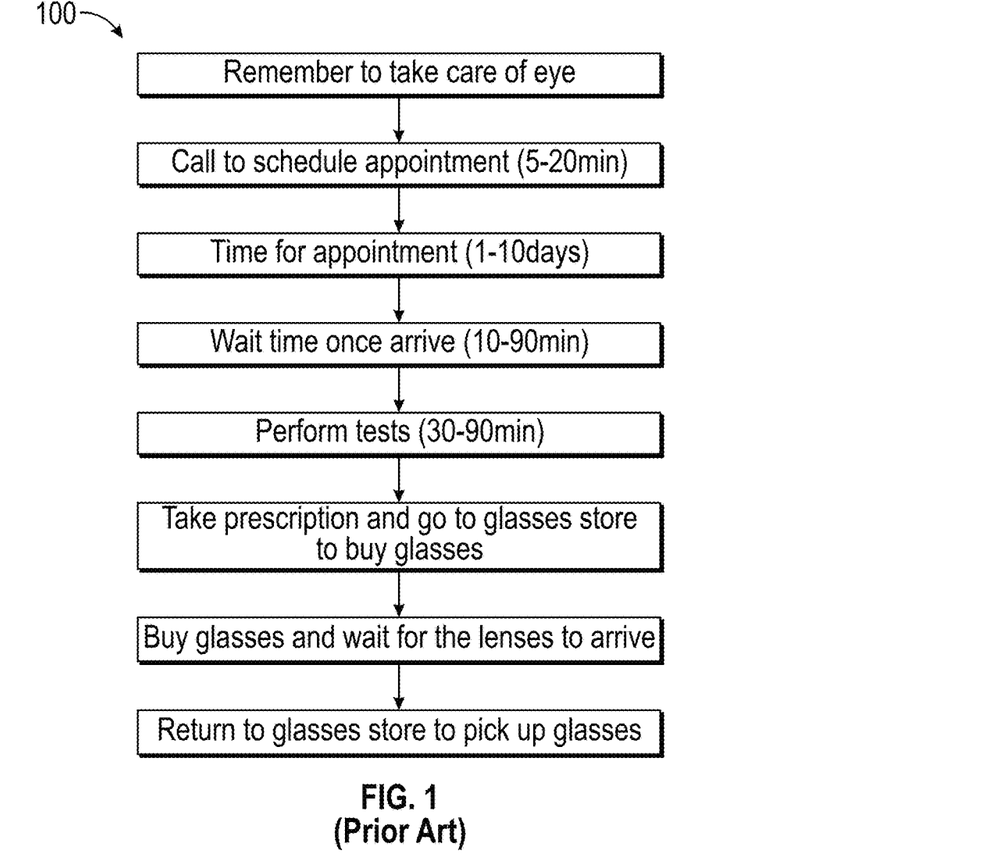
FIG. 1 Current process for getting eye glasses
Figure 2:
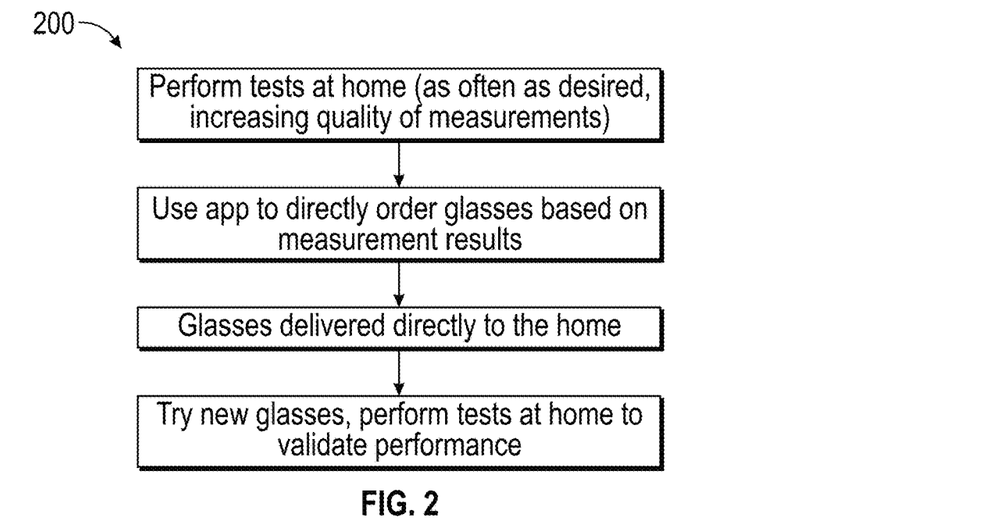
FIG. 2 Proposed example of process for obtaining eyeglasses
Figure 3:
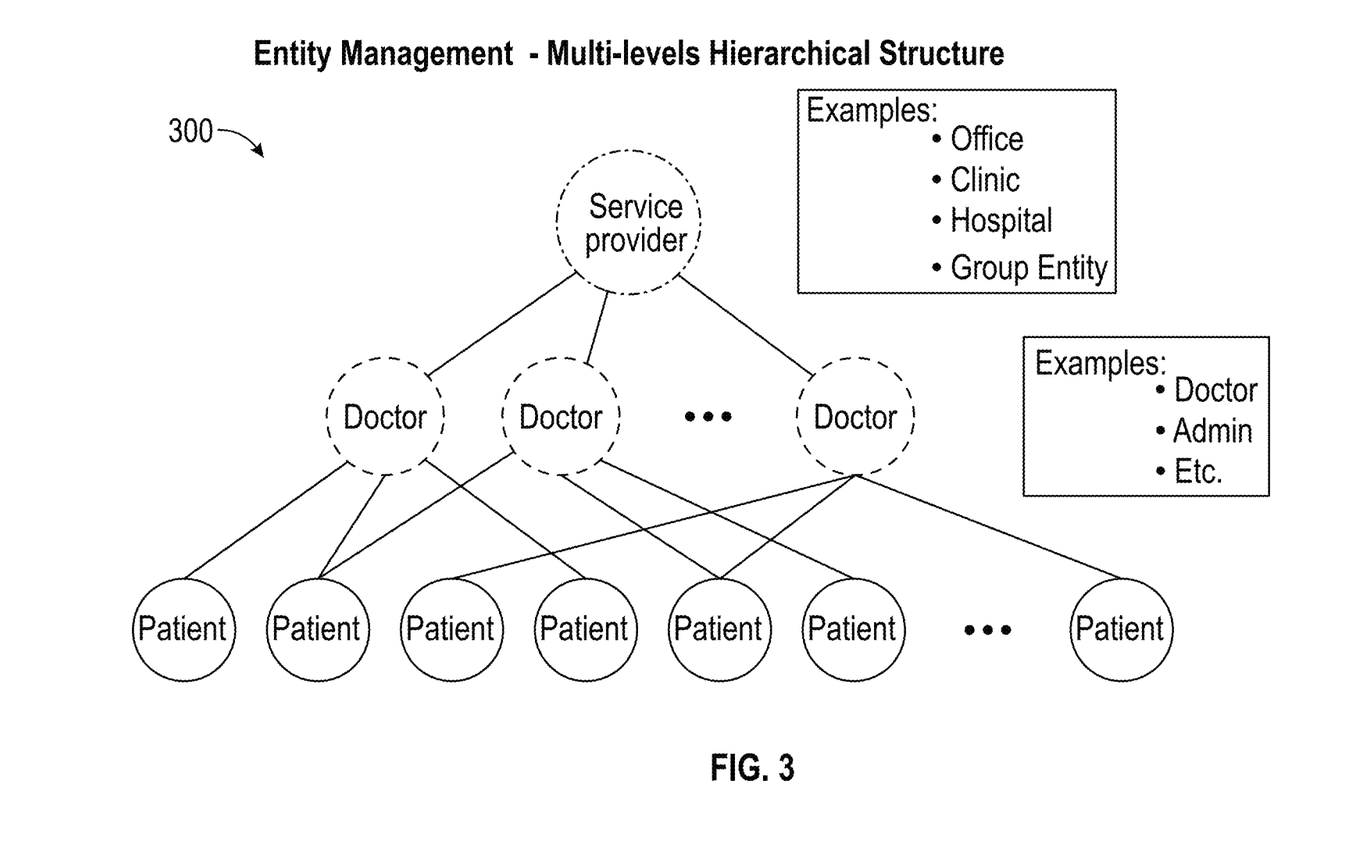
FIG. 3 Example of proposed enterprise model
Figure 4A:
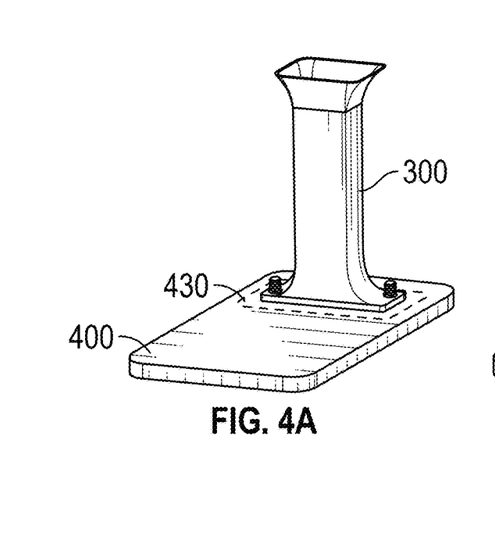
FIG. 4A-C Example of display resolution measurement implementation
Figure 4B:
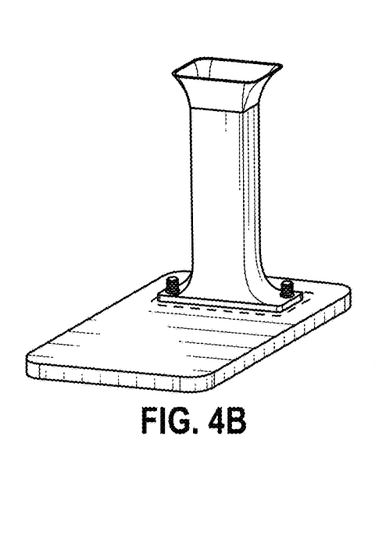
Figure 4C:
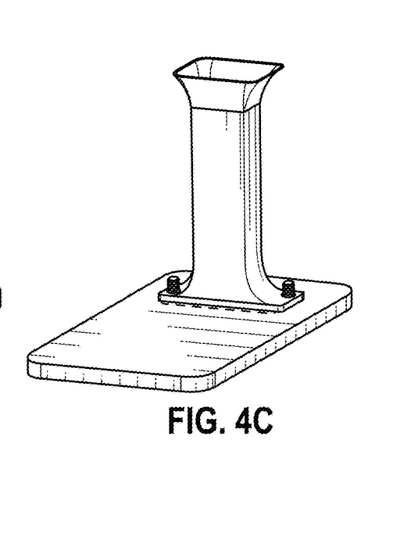

In an embodiment of the invention, a resolution measurement is performed on a display, for example, of a smartphone. The user is asked to attach the device used in the refraction or vision test. The user is then presented with a shape on the display that is the same shape and aspect ratio of the attached device. The user then adjusts the size and location of the displayed shape until is matches the outline of the base of the attached device. FIG. 4 illustrates an example of an implementation of this method. FIG. 4A shows a device attached to a smartphone display where the outlined shape presented to the user is too large compared to the base of the attached device. FIG. 4C shows a device attached to a smartphone display where the outlined shape presented to the user is too small compared to the base of the attached device. FIG. 4.b. shows a device attached to a smartphone display where the outlined shape presented to the user is the right size of the base of the attached device. At that point the user may indicate the match and the size of the shape is then measured in pixels. As the size of the device is well known the display resolution (PPI—pixels per inch) can be calculated according to:

$$PPI = \frac{d_p}{D_D}$$

Where $d_p$ is the presented shape final match size in pixels taken from the drawn shape on the display, and $D_D$ is the well known shape size of the base of the device in inches.

Figure 5:
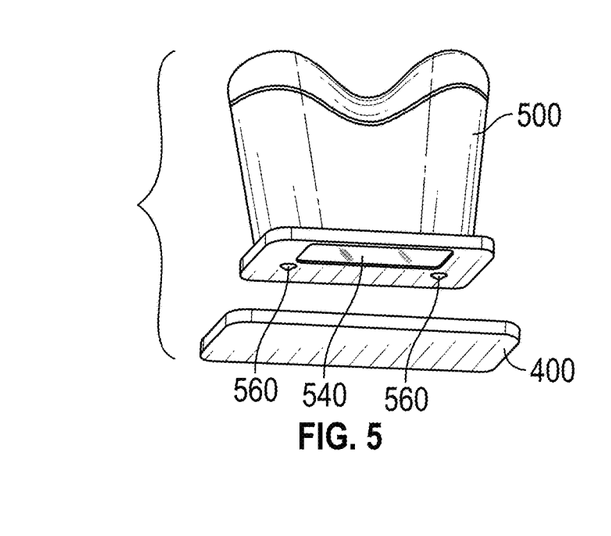
FIG. 5 Example of display resolution measurement implementation

In another embodiment of the invention the resolution measurement could be performed by using sensors rather than by user input. In a suggested implementation a measurement device could be mounted on a frame that includes at least two touch points or the device itself has embedded on itself at least two touch points. These touch points are made of a material that allows interaction with a touch screen. An example would be a rubber dome attached to a slightly conductive plastic frame. The touch points are then attached to the display which includes a touch screen (e.g. as on a smartphone). The display then senses the two touch points and registers the pixel values for each of the points. The distance between the points could then be calculated according to the following formula:

$$d_p = \sqrt{(y_2-y_1)^2 - (x_2-x_1)^2}$$

Where $(x_{1,2}, y_{1,2})$ are touch points 1 and 2 coordinates sensed on the screen. The PPI could then be calculated using the same formula above with $D_D$ the distance in inches between the touch points on the device. In another embodiment of the invention, three touch points or more could be implemented such that the resolution could be measured in more than one direction.

FIG. 5. shows and example implementation of the proposed embodiment. In the figure, an attachment device is held in a frame which has two touch points. The distance of between which is well known. The device with the frame and the touch points are then attached to a touch capable display. The display then senses the touch points and can determine the touch pixels. The above procedure for calculating PPI can then be followed.

In another embodiment of the invention a method for aberration correction is presented. In particular, distortion type aberration. The distortion is mapped spatially, and the distortion map is used to create pre-distorted images that when viewed through the distorting optics present clear images to the user. The distortion map could be obtained through simulation or empirically. Simulation of the distortion map could be achieved through ray tracing or other calculation (analytic or numerical). Empirical mapping could be done for example by observing through the optical device and presenting a lines of varying distances and assigning a curvature to each line as a function of the distance from the center in order to get a straight line when observed through the optical system. In other implementations, grids or dots may be used for the mapping instead of lines, in which case the curvature is used to straighten the grid or create an equidistant dots array, respectively. In an example implementation the curvature would be matched to a radius of a circle. In another implementation the curves will be matched to a polynomial expansion of a function. A best fit could be performed to match the curvature as a function of distance from the center. This could in turn be used to correct presented images to the user through the optical device. In an example implementation, for centrally symmetric images, the measurement of the distance could be bilateral (between two concentric lines) rather than single distance to the center. In a simplified implementation, where the presented image is intended to be of line bars, the curvature could be taken as uniform for the entire bar based for example on the curvature of the center of the bar. This could be done to simplify having to create different curvatures for the sides of the bar. This approximation works well if the bar thickness is small relative to the radius of curvature.

Figure 6A:
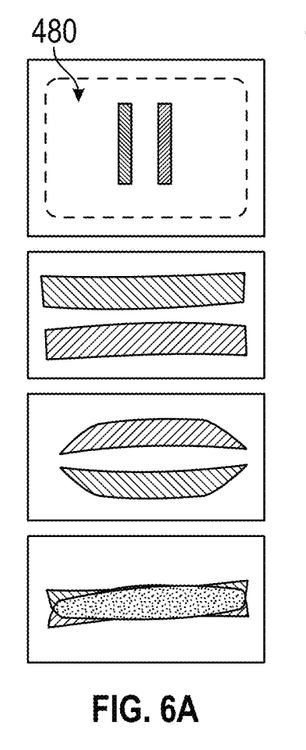
FIG. 6A-C Example of image distortion correction
Figure 6B:
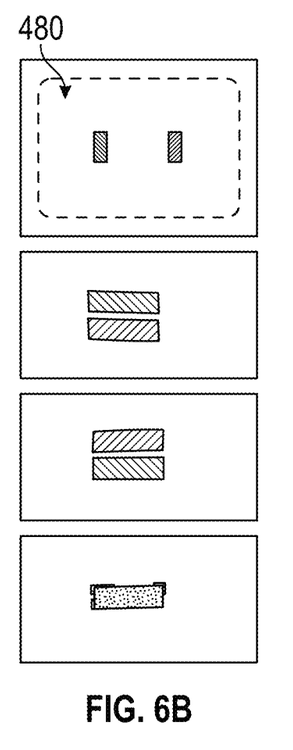
Figure 6C:
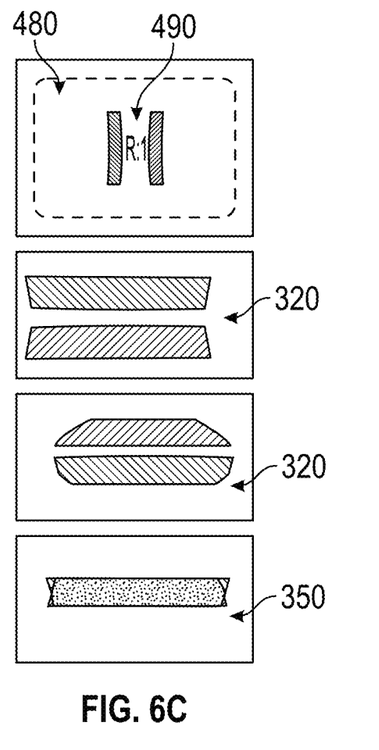
Figure 7:
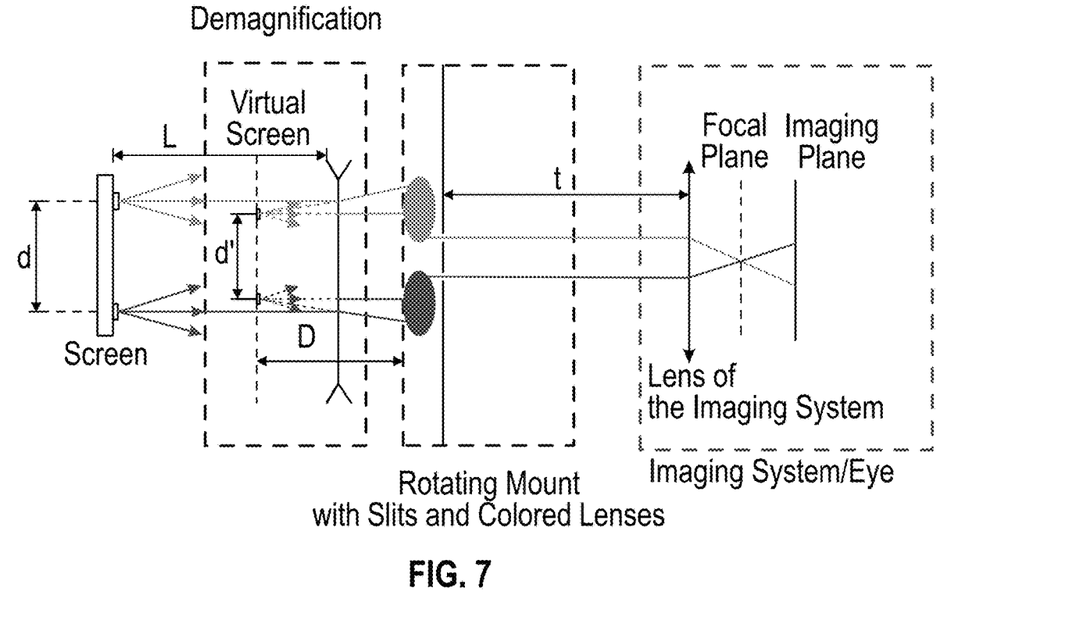
FIG. 7 depicts a first lens used for demagnification, a first and second lens each defining one slit, with the second lens of a different color from the third lens.

FIG. 6 presents an illustration of an example implementation of the distortion correction. The figure uses two color bars as the displayed image. This image is useful to showcase the distortion correction as well as is used in the refraction measurement device in a PVT system. The figure presents on the first line the image presentation on the display. The second and third lines present the two bars as can be seen through the attached device in two different positions of the bars on the display. The last line shows the case where, thought the attached device, the lines seem to be overlapping. This is the case for 0D refraction as an example. It shows the potential ambiguity of the overlapping condition that is required in the refraction measurement of [PVT patent]. FIG. 6A shows the distortion present in the device where the image on the display is what is expected through the system without any correction. This figure shows the fact that straight lines on the display correspond to curved lines through the device optics. This would then lead to errors and ambiguity for the user while they are observing the image and performing the refraction test. FIG. 6B presents a form of prior art of controlling the distortion in the image. The solution used was reduction of the bar length to minimize the effect of the curvature of the lines due to the distortion of the optical system. The disadvantages of this method are clear as the curvature has not been diminished but rather is only less apparent. The shorter length of the lines causes many users to have problems observing the lines and performing the test (aligning the bars). FIG. 6.c. presents an implementation of the solution of the current invention where the lines on the display are pre-distorted to create a clear image through the optics. The procedures describe hitherto are used to create a mapping of the curvature of the bar as a function of the distance between the bars to create straight lines as they are observed through the optics of the attached device (lines 2-4 in the figure).

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

Disclosed items include:

1. A method to measure refraction error of an optical system, the method comprising the steps of:

a) using a first lens for demagnification;

b) using a second and third lens, with the second and third lens each defining one slit; and wherein the second lens is of a different color as compared to the third lens;

c) using a view screen to project a first line through the first and second lenses and using the view screen to project a second line through the first and third lenses, wherein the first and second lines are pre-distorted so as to project relatively straight lines as perceived by a user;

d) using meridian angles to rotate the first and second lines projected by the view screen;

e) using a first meridian angle to initially dispose the first and second lines projected by the view screen and using the optical system being tested to adjust the first line and second line to alignment to derived a first distance of line movement for the first meridian angle;

f) using a second meridian angle, the second meridian angle being a predefined angular difference from the first meridian angle; adjusting the first line and second line, as perceived by the optical system being tested, such that the first and second lines are aligned to derived a second distance of line movement for the second meridian angle;

g) using the first and second distance of line movement in conjunction with the first and second meridian angles, to derive the refractor error of the optical system.

2. The method of 1 further including the step of projecting a view port indicia (430) upon the view screen; the user adjusting the view port screen to comport with a view port of the first and second lens lines.

3. The method of 2 further including the step of calculating a display resolution of the display screen by use of the size of the view port screen size, as adjusted by the user.

4. The method of 2 further including the step of calculating display resolution by $$PPI = \frac{d_p}{D_D}$$

5. A system to measure refraction error of an optical system, the system comprising:
   a) a first lens used for demagnification;
   b) a second and third lens, with the second and third lens each defining one slit; and wherein the second lens is of a different color as compared to the third lens;
   c) a view screen to project a first line through the first and second lenses and using the view screen to project a second line through the first and third lenses, wherein the first and second lines are pre-distorted so as to project relatively straight lines as perceived by a user;
   d) using meridian angles to rotate the first and second lines projected by the view screen;
   e) a first meridian angle employed to initially dispose the first and second lines projected by the view screen and using the optical system being tested to adjust the first line and second line to alignment to derived a first distance of line movement for the first meridian angle;
   f) a second meridian angle being a predefined angular difference from the first meridian angle; adjusting the first line and second line, as perceived by the optical system being tested, such that the first and second lines are aligned to derived a second distance of line movement for the second meridian angle;
   g) using the first and second distance of line movement in conjunction with the first and second meridian angles, to derive the refractor error of the optical system.

6. The system of 5 further comprising of a view port indicia (430) disposed upon the view screen; the view port screen adjusted to comport with a view port of the first and second lens lines.

7. The system of 5 wherein display resolution is derived by use of the size of the view port screen size.

8. The system of 6 wherein display resolution is derived by $$PPI = \frac{d_p}{D_D}.$$

What is claimed is:

1. A method to measure refraction error of an optical system, the method comprising the steps of:
   a) using a first lens for demagnification;
   b) using a second and third lens, with the second and third lens each defining one slit; and wherein the second lens is of a different color as compared to the third lens;
   c) using a view screen to project a first line through the first and second lenses and using the view screen to project a second line through the first and third lenses, wherein the first and second lines are pre-distorted so as to project relatively straight lines as perceived by a user;
   d) using meridian angles to rotate the first and second lines projected by the view screen;
   e) using a first meridian angle to initially dispose the first and second lines projected by the view screen and using the optical system being tested to adjust the first line and second line to alignment to derived a first distance of line movement for the first meridian angle;
   f) using a second meridian angle, the second meridian angle being a predefined angular difference from the first meridian angle; adjusting the first line and second line, as perceived by the optical system being tested, such that the first and second lines are aligned to derived a second distance of line movement for the second meridian angle;
   g) using the first and second distance of line movement in conjunction with the first and second meridian angles, to derive the refractor error of the optical system.

2. The method of claim 1, further including the step of projecting a view port indicia (430) upon the view screen; the user adjusting the view port screen to comport with a view port of the first and second lens lines.

3. The method of claim 2, further including the step of calculating a display resolution of the display screen by use of the size of the view port screen size, as adjusted by the user.

4. A system to measure refraction error of an optical system, the system comprising:
   a) a first lens used for demagnification;
   b) a second and third lens, with the second and third lens each defining one slit; and wherein the second lens is of a different color as compared to the third lens;
   c) a view screen to project a first line through the first and second lenses and using the view screen to project a second line through the first and third lenses, wherein the first and second lines are pre-distorted so as to project relatively straight lines as perceived by a user;
   d) using meridian angles to rotate the first and second lines projected by the view screen;
   e) a first meridian angle employed to initially dispose the first and second lines projected by the view screen and using the optical system being tested to adjust the first line and second line to alignment to derived a first distance of line movement for the first meridian angle;
   f) a second meridian angle being a predefined angular difference from the first meridian angle; adjusting the first line and second line, as perceived by the optical system being tested, such that the first and second lines are aligned to derived a second distance of line movement for the second meridian angle;
   g) using the first and second distance of line movement in conjunction with the first and second meridian angles, to derive the refractor error of the optical system.

5. The system of claim 4, further comprising of a view port indicia (430) disposed upon the view screen; the view port screen adjusted to comport with a view port of the first and second lens lines.

6. The system of claim 4, wherein display resolution is derived by use of the size of the view port screen size.

7. The system of claim 4, wherein the second lens is the same color as the third lens.

* * * * *